United States Patent [19]

Suda et al.

[11] 3,953,521

[45] Apr. 27, 1976

[54] PROCESS FOR THE CONTINUOUS PRODUCTION OF DIHYDROPEROXIDES

[75] Inventors: Hideaki Suda, Takaishi; Iwao Dohgane, Nishinomiya; Takashi Chinuki, Toyonaka; Kenji Tanimoto; Hirokazu Hosaka, both of Minoo; Yukimichi Nakao, Kobe; Yuji Ueda, Izumiotsu; Seiya Imada, Sakai; Hideki Yanagihara, Toyonaka; Kunihiko Tanaka, Ibaragi, all of Japan

[73] Assignee: Sumitomo Chemical Company, Limited, Osaka, Japan

[22] Filed: June 27, 1975

[21] Appl. No.: 590,930

Related U.S. Application Data

[63] Continuation of Ser. No. 388,477, Aug. 15, 1973, abandoned.

[30] Foreign Application Priority Data

Aug. 23, 1972   Japan.............................. 47-84733

[52] U.S. Cl............................................. 260/610 B
[51] Int. Cl.$^2$................................. C07C 179/06

[58] Field of Search................................. 260/610 B

[56] References Cited
UNITED STATES PATENTS

| | | | |
|---|---|---|---|
| 2,632,026 | 3/1953 | Conner | 260/610 A |
| R23,916 | 12/1954 | Lorand | 260/610 B |

FOREIGN PATENTS OR APPLICATIONS

| | | | |
|---|---|---|---|
| 727,498 | 4/1955 | United Kingdom | 260/610 B |

*Primary Examiner*—James O. Thomas, Jr.
*Assistant Examiner*—W. B. Lone
*Attorney, Agent, or Firm*—Stevens, Davis, Miller & Mosher

[57] ABSTRACT

Meta-and/or paradiisopropylbenzene dihydroperoxides are continuously produced by oxidizing meta-and/or paradiisopropylbenzenes in liquid phase through contact with oxygen or a gas containing oxygen, while keeping the concentration of meta-and/or paradiisopropylbenzene monohydroperoxides of the oxidation product solution in a range of 20 to 40% by weight.

4 Claims, 1 Drawing Figure

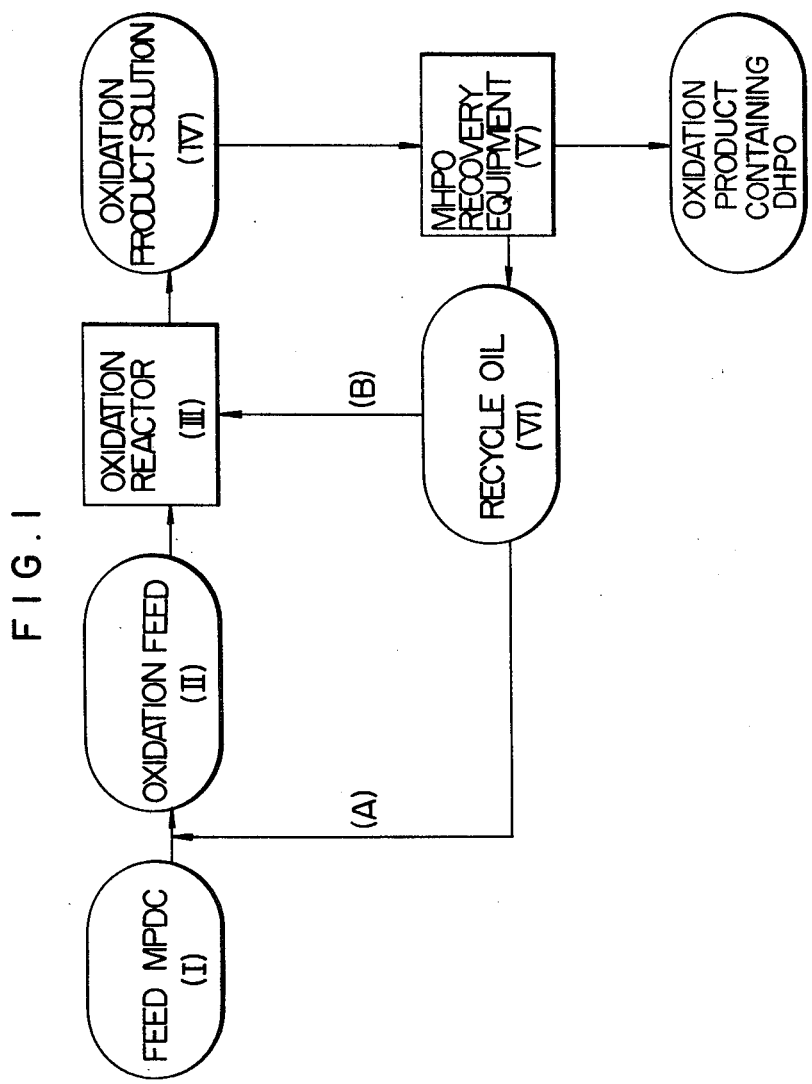
F I G. I

PROCESS FOR THE CONTINUOUS PRODUCTION OF DIHYDROPEROXIDES

This is a continuation of application Ser. No. 388,477 filed Aug. 15, 1973 now abandoned.

This invention relates to a process for continuously producing meta-and/or paradiisopropylbenzene dihydroperoxides.

When meta-and/or paradiisopropylbenzene (which will be hereinafter referred to as MPCD) is oxidized in liquid phase through contact with oxygen or a gas containing oxygen, several kinds of hydroperoxides (which will be hereinafter referred to as HPO) are produced in addition to the desired meta-and/or paradiisopropylbenzene dihydroperoxide (which will be hereinafter referred to as DHPO), and it is not possible to selectively produce only DHPO from MPDC.

For example, a considerable amount of meta-and/or paradiisopropylbenzene monohydroperoxides (which will be hereinafter referred to as MHPO), which can be considered as a precursor of CHPO, is formed in the oxidation product solution. Therefore, it is desirable, even from an economical viewpoint, to recover the unreacted feed material MPDC or intermediate product MHPO from the oxidation product solution, and to return them to the oxidation reaction. Said continuous oxidation reaction and recovery and recycle of some of components constituting the oxidation product solution to the oxidation reaction are well known. Further, it is well known to carry out the oxidation reaction particularly by keeping the concentration of MHPO at 45 % by weight of higher (the percentage will be hereinafter referred to as "% by weight"), as disclosed in Japanese Pat. Publication No. 428/56.

However, the present inventors have found through trace tests of the well known processes and experiences of carrying out similar reactions that, to obtain DHPO in good yield in the oxidation reaction of MPDC, it is not always necessary to keep the concentration of MHPO at 45 % or higher as so far known, but a very good result can be obtained by keeping the concentration rather low.

That is to say, as a result of studies of and research upon of the oxidation reaction, particularly its kinetics, for example, rate constant and order of reaction of each elementary reaction, the present inventors have drawn the following conclusion. In the DHPO formation of said oxidation reaction, the reaction for converting MHPO to DHPO is a rate-determining step, and thus an increase in the MHPO concentration of the oxidation product solution will be an important factor for increasing the rate of formation of DHPO, but conversion of MHPO to compounds other than DHPO is promoted at the same time. Therefore, it is not always preferable to keep MHPO at a higher concentration. In other words, there is such an area that both rate of DHPO formation and selectivity of the reaction reach maximum.

As a result of further study on the oxidation reaction in view of the foregoing facts, the present inventors have found that the most favorable results for the production of DHPO can be obtained, when the oxidation reaction is carried out by keeping the MHPO concentration of the oxidation product solution in a range of 20 to 40 %, preferably 25 to 35 %.

The MHPO concentration in the present invention means a concentration of MHPO in the final oxidation product taken out of an oxidation reactor when the oxidation reaches equilibrium, usually a maximum concentration of MHPO in the oxidation system.

That is, the present inventors have found that when the MHPO concentration of the oxidation product solution is kept at more than 40 % in the continuous oxidation reaction, the rate of conversion of MHPO to DHPO is not so high as the rate of conversion of MPDC to MHPO, and thus MHPO is consequently accumulated at a high concentration. In other words, the fact that there is more than 40 % of MHPO in the oxidation product solution when an equilibrium is established reveals that the rate of conversion of MHPO to DHPO is not so high. So is the case, when the MHPO concentration is less than 20 %. In this case, there prevails a just reversed situation. That is, the rate of conversion of MHPO to DHPO is so high that MHPO is not so much accumulated, and consequently an equilibrium is established even at such a low MHPO concentration as 20 %. Therefore, the MHPO concentration is critical for the continuous production of DHPO, that is, if the MHPO concentration is kept at more than 40 % in the oxidation product solution, the rate of conversion to DHPO turns lower, and if the MHPO concentration is kept at less than 20 %, the rate of conversion to DHPO turns too much higher.

However, in the latter case, it is impossible, in view of the rate of conversion of MPDC to MHPO, to increase the rate of conversion of MHPO to DHPO to keep the MHPO concentration at less than 20 %, and the MHPO concentration of 20 % is nearly a limit on the reaction where MPDC coexists, that is, in the continuous oxidation reaction. If the reaction is carried out by force while keeping the MHPO concentration at less than 20 %, other reactions than the conversion of MHPO to DHPO are much accelerated, and the selectivity of DHPO from MHPO is decreased due to the conversion of MHPO to compounds other than DHPO. Consequently, the rate of DHPO formation cannot be increased. That is, even if the reaction can be carried out while keeping the MHPO concentration at lesss than 20 %, such reaction will not give any substantial benefit to the formation of DHPO.

For the foregoing reasons, it is most desirable for formation of DHPO from the viewpoint of kinetics as well as yield to carry out the oxidation while keeping the MHPO concentration of the oxidation product solution in a range of 20 to 40 %. The present invention is thus quite distinguished from such prior art where the MHPO concentration of 45 % or higher in the oxidation product solution is preferred for the oxidation reaction.

The present invention is based on the present inventor's new findings that the consecutive reactions for converting MPDC to DHPO through MHPO are oxidation reactions having such a tendency that higher yield is essentially assured by lower conversion, and the ratedetermining step of the reactions resides in the step of converting MHPO to DHPO.

To control the MHPO concentration to said desirable range in the oxidation product solution, it is necessary to set conditions of the oxidation reaction to maintain the MHPO concentration at a stage where MHPO recovered from the oxidation product solution according to the well known method is again supplied to the oxidation reaction solution. The conditions of oxidation reaction are qualitatively and quantitatively freely changeable factors such as reaction temperature, pressure, time, proportion of oil layer to water layer, catalyst, pH, additives, etc., and all the well known factors as to the oxidation reaction conditions can be applied to the purpose of the present invention.

Even after a solution containing unreacted MPDC or MHPO recovered from the oxidation product solution or freshly made-up feed MPDC or other necessary compounds are all added, the MHPO concentration of the oxidation reaction solution can be also kept with ease within the desirable range, for example, by controlling the reaction temperature or reaction time. It is not very difficult to continuously carry out the oxidation reaction while keeping the MHPO concentration within said desirable definite range, but it is possible to control the amount of MHPO in the materials fed to the reaction system in order to effect a temporary adjustment to a desired MHPO concentration. One embodiment of the oxidation conditions in order to keep the MHPO concentration within a range mentioned above will be given as follows.

The reaction may be carried out at a temperature of 80° to 130°C, preferably about 100°C under a pressure of atmospheric to 10 atm, when compressed air is used, for 1 to 30 hours, usually 10 to 20 hours. A proportion of an aqueous component to an oily component constituting the oxidation system is from 1 : 10 to 10 : 1, usually one to one or more. The reaction is carried out in the presence of an alkali as a catalyst for adjusting the pH to 5 to 12, usually carried out under neutral to weak alkaline state. In some cases, other additives may be added to the oxidation system.

Now, the present invention will be described by way of the accompanying drawing.

The FIGURE is a schematic flow diagram showing one embodiment of the flow according to the present invention.

In the FIGURE, an oxidation feed (II) consisting of feed MPDC (I) and unreacted MPDC or MHPO recovered from the oxidation product solution is fed to an oxidation reactor (III), wherein the oxidation reaction is carried out. The oxidation product solution (IV) is withdrawn from the oxidation reactor (III) after the completion of reaction and transferred to a MHPO recovery equipment (V), wherein a recycle oil (VI) containing mainly MHPO and unreacted MPDC is recovered from the oxidation product solution. The recycle oil (VI) is joined with the feed MPDC (I) through a line (A) and/or fed directly to the oxidation reactor (III) through a line (B). Thus, the recycle oil (VI) is recycled to the oxidation reaction system anyway.

The present invention will be summarized, if referred to the embodiment as shown in the Figure, to be a process for continuously producing meta-and/or paradiisopropylbenzene dihydroperoxides, characterized by carrying out the oxidation reaction while keeping on MHPO concentration in a range of 20 to 40 % in the oxidation reactor (III) by adjusting the conditions of the oxidation reaction in the oxidation reactor (III), and the amount of recycle oil through the line (A) and/or (B). The present invention can be also applied to the production of dihydroperoxides of alkylbenzene in a process for producing resorcinol and hydroquinone from alkylbenzenes.

Now, the present invention will be described in detail by way of the Examples. In Examples, a part is by weight, and a part by volume is a capacity corresponding to the part by weight.

EXAMPLE 1

The oxidation reactor used in the Examples is a stainless steel cylindrical vessel having a capacity of 300 parts by volume, provided with a means of dispersing gas and liquid, a thermometer, a gas inlet pipe and a condenser for condensing vapors entrained by excess gas. The reactor is further provided with a feed inlet for feed materials including recycle oil and an outlet for discharging the oxidation product from the reactor, whereby feeding of the reaction feed materials and discharging of the product can be carried out continuously.

To the reactor are fed 170 parts of MPDC (a mixture of meta-and paradiisopropylbenzenes at a ratio of meta to para of about 6 : 4), 20 parts of water and 25 parts of MPDC oxidation product containing 18 parts of equivalent MHPO as a reaction initiator. The reactor is heated to 95°C, and the reaction is carried out by passing air compressed to 3 atm through the reactor at a rate of 20,000 parts by normal volume per hour and adding to the reactor 10.5 parts by volume of an aqueous solution containing 0.25 parts of caustic soda per hour.

After 5 hours from the start of reaction, the MHPO concentration and DHPO concentration of the reaction solution reach 44.8% and 10.5 %, respectively, and after 7 hours, the MHPO concentration and DHPO concentration reach 46.8 % and 26.0 %, respectively. Then, the continuous reaction is carried out by recovering MPDC and MHPO from the oxidation product solution, adding fresh MPDC to the recovered MPDC and MHPO, and continuously feeding the resulting feed solution and an aqueous 0.5 % caustic soda solution at rates of 40 parts by volume and 15 parts by volume, respectively, per hour. After the start of continuous reaction, the MHPO concentration and DHPO concentration of the oxidation product solution leaving the reactor are 37.7 % and 20.8 %, respectively. After 50 hours from the start of the continuous reaction, the MHPO concentration and DHPO concentration of the effluent oxidation product solution are 34.0 % and 19.2 %, respectively. After 100 hours, the MHPO concentration and DHPO concentration are 34.2 % and 19.0 %, respectively. Likewise, after 500 hours but just before the stop of reaction, the MHPO concentration, DHPO concentration and unreacted MPDC concentration are 34.5 %, 19.4 % and 17.9 %, respectively. Throughout the oxidation reaction, the MHPO concentration is stabilized in a range of 34 to 35 %, and the DHPO concentration is stabilized in a range of 19.0 to 19.6 % after 20 hours from the start of the continuous reaction. Further, the unreacted MPDC concentration falls in a range of 17.6 to 19.3 %.

The MHPO concentration and MPDC concentration of the solution to be fed to the oxidation reactor are in ranges of 32.2 to 33.1 % and 37.4 to 38.6 %, respectively, throughout the oxidation reaction. An average material balance for 400 hours where the reaction is in equilibrium and stable before the stop of the continuous oxidation reaction is a ratio of 105.4 parts of effluent product solution to 100 parts of feed solution, exclusive of water.

To make the effect of the present invention much clearer, the following comparative test was carried out. The comparative test reveals that the oxidation at an MHPO concentration of more than 40 % of the oxidation reaction solution produces disadvantageous effects upon the rate of DHPO formation and yield of DHPO.

COMPARATIVE EXAMPLE

The oxidation reaction is carried out under the same feeding and reaction conditions as in Example 1, using the same reactor as in Example 1, except that the reaction temperature is 90°C. After 20 hours from the start of reaction, the reaction is changed to a continuous reaction at the time when the MHPO concentration and DHPO concentration of the product solution reach 52.3 % and 9 %, respectively. That is, the continuous reaction is carried out by recovering MPDC and MHPO from the effluent oxidation product solution, adding fresh MPDC to the recovered MPDC and MHPO, and continuously feeding the resulting feed solution and the aqueous 0.5 % caustic soda solution to the oxidation reactor at rates of 50 parts by volume and 20 parts by volume, respectively, per hour. No great difference is observed between the composition of the product solution just after 30 hours from the start of continuous reaction and that just after 300 hours but just before the stop of the continuous reaction, and the composition of the product solution is maintained almost stably during the period of the continuous oxidation. The MHPO concentration and MPDC concentration of the feed solution to the oxidation reactor are in ranges of 47.6 to 49.2 % and 38.0 to 39.4 %, respectively, throughout the period of the oxidation reaction. Likewise, the oxidation product solution contains, on average, 50.1 % MHPO, 9.7 % DHPO and 21.8 % MPDC. The material balance is a ratio of 104.7 parts of the oxidation product solution to 100 parts of the feed solution, exclusive of water.

In the reaction using the same reactor, about 120 parts of DHPO is obtained from 100 parts of MPDC in the case of Example 1, and about 70 parts of DHPO is obtained from 100 parts of MPDC in the case of the comparative example. The rate per hour of DHPO formation, is about 62 in the case of the comparative example, when the rate per hour of DHPO of Example 1 is presumed to be 100.

It is apparent from the foregoing comparative example that the present invention is industrially more distinguished over the prior art.

EXAMPLE 2

The oxidation reaction is carried out by using the same oxidation reactor as in Example 1, feeding the same reaction initiator as in Example 1, heating the reactor to 115°C, and passing air compressed to 7 atm through the reactor at a rate of 28,000 parts by normal volume per hour and adding thereto 18.7 parts by volume of an aqueous solution containing 0.37 parts of caustic soda per hour. After 10 hours from the start of reaction, continuous reaction is carried out by supplying a feed solution containing MPDC and MHPO recovered from the oxidation product solution containing 25.5 ± 0.4 % MHPO and 60.0 ± 2 % MPDC or freshly made-up MPDC at a rate of 30 parts by volume per hour and an aqueous 0.7 % caustic soda solution at a rate of 28 parts by volume per hour to the oxidation reactor. MHPO is stabilized in the oxidation reactor at a considerably early time after the start of the continuous reaction, but the composition of the solution changes from time to time. That is, the solution has 45.2 % MHPO, 18.2 % DHPO and 19.1 % unreacted MPDC after the start of the continuous reaction, but the contents of MHPO and the unreacted MPDC are gradually decreased, whereas the content of DHPO is increased. After 60 hours from the start of continuous reaction, the solution within the oxidation reactor contains 25–26 % MHPO, 46–47 % DHPO and 3–4 % unreacted MPDC. Thereafter, the contents of MHPO, DHPO and MPDC are stabilized and undergo almost no changes at all. For example, the solution contains 25.2 % MHPO, 46.1 % DHPO and 3.8 % unreacted MPDC just before the stop of reaction after 500 hours from the start of the continuous reaction.

The material balance of the effluent product solution to the feed solution, exclusive of gases and water, from the start of discharging the oxidation product solution from the reactor till the stop of the continuous reaction is 107.1 parts of the effluent to 100 parts of the feed.

What is claimed is:

1. A process for continuously producing meta- and paradiisopropylbenzene dihydroperoxides by oxidation of the mta- and paradiisopropylbenzenes in liquid phase through contact with oxygen or a gas containing oxygen, which comprises effecting the oxidation while keeping the concentration of meta- and paradiisopropylbenzene monohydroperoxides of the oxidation product solution in a range of 20 to 40% by weight, the oxidation being carried out at a temperature of 80° to 130°C for 1 to 30 hours and at a pressure from atmospheric to 10 atmospheres maintained by feeding compressed air and in the presence of an alkali as a catalyst for adjusting the pH from 5 to 12.

2. A process according to claim 1, wherein the concentration of meta-and paradiisopropylbenzene monohydroperoxides is in a range of 25 to 35 % by weight.

3. A process for continuously producing m- and p-diisopropylbenzene dihydroperoxides by feeding m- and p-diisopropylbenzenes to an oxidation zone, in which the diisopropylbenzenes are oxidized in liquid phase through contact with oxygen or a gas containing oxygen, transferring the resulting oxidation product solution to a monohydroperoxide recovery zone, in which a recycle oil mainly containing m- and p-diisopropylbenzene mono-hydroperoxides and unreacted m- and p-diisopropylbenzenes is separated from the oxidation product mainly containing the dihydroperoxides, and recycling the recycle oil directly to the oxidation zone, which comprises effecting the oxidation while keeping the concentration of the diisopropylbenzene monohydroperoxides of the oxidation product solution in a range of 20 to 40% by weight, the oxidation being carried out at a temperature of 80° to 130°C for 1 to 30 hours and at a pressure from atmospheric to 10 atmospheres maintained by feeding compressed air and in the presence of an alkali as a catalyst for adjusting the pH from 5 to 12.

4. A process for continuously producing m- and p-diisopropylbenzene dihydroperoxides by feeding m- and p-diisopropylbenzenes to an oxidation zone, in which the diisopropylbenzenes are oxidized in liquid phase through contact with oxygen or a gas containing oxygen, transferring the resulting oxidation product solution to a monohydroperoxide recovery zone, in which a recycle oil mainly containing m- and p-diisopropylbenzene mono-hydroperoxides and unreacted m- and p-diisopropylbenzenes is separated from the oxidation product mainly containing the dihydroperoxides, and recycling the recycle oil together with the feed diisopropylbenzenes to the oxidation zone, which comprises effecting the oxidation while keeping the concentration of the diisopropylbenzene monohydroperoxides of the oxidation product solution in a range of 20 to 40% by weight, the oxidation being carried out at a temperature of 80° to 130°C for 1 to 30 hours and at a pressure from atmospheric to 10 atmospheres maintained by feeding compressed air and in the presence of an alkali as a catalyst for adjusting the pH from 5 to 12.

* * * * *